US012650387B1

(12) United States Patent
Ioffe et al.

(10) Patent No.: US 12,650,387 B1
(45) Date of Patent: Jun. 9, 2026

(54) SYSTEM AND METHOD FOR EVALUATING AND DETERMINING COLOR IN GEMSTONES

(71) Applicant: SARINE TECHNOLOGIES LTD., Hod Hasharon (IL)

(72) Inventors: Zvi Ioffe, Kfar Saba (IL); Ariel Danan, Tel Aviv (IL); Amiram Eldar, Jerusalem (IL)

(73) Assignee: SARINE TECHNOLOGIES LTD. (IL)

( * ) Notice: Subject to any disclaimer, the term of this patent is extended or adjusted under 35 U.S.C. 154(b) by 0 days.

(21) Appl. No.: 18/400,134

(22) Filed: Dec. 29, 2023

Related U.S. Application Data

(63) Continuation of application No. 17/393,654, filed on Aug. 4, 2021, now Pat. No. 11,892,412, which is a
(Continued)

(51) Int. Cl.
  *G01N 21/87* (2006.01)
  *G01N 21/25* (2006.01)
  (Continued)

(52) U.S. Cl.
  CPC ........... *G01N 21/87* (2013.01); *G01N 21/251* (2013.01); *G01N 21/6456* (2013.01); *G01N 33/389* (2024.05); *G06T 7/11* (2017.01); *G06T 7/90* (2017.01); *H04N 23/54* (2023.01); *H04N 23/56* (2023.01); *H04N 23/695* (2023.01);
  (Continued)

(58) Field of Classification Search
  None
  See application file for complete search history.

(56) References Cited

U.S. PATENT DOCUMENTS

| | | | |
|---|---|---|---|
| 6,239,867 B1 | 5/2001 | Aggarwal | |
| 2003/0107722 A1 | 6/2003 | Klingler | |

(Continued)

OTHER PUBLICATIONS

Wang Dadong et al., "Automated Opal Grading by Imaging and Statistical Learning", IEEE Transactions on Systems, MAN, and Cybernetics: Systems, IEEE, Piscataway, NJ, USA, vol. 46, No. 2, Feb. 1, 2016, pp. 185-201.
(Continued)

*Primary Examiner* — James M Anderson, II
(74) *Attorney, Agent, or Firm* — ISUS INTELLECTUAL PROPERTY PLLC; Anthony Jason Mirabito

(57) ABSTRACT

A system for the automatic grading of a cut/polished gemstone (SUT) includes an enclosure with a stage for mounting the cut/polished SUT. The enclosure further includes one or more sources of broadband visible (BBV) light, the sources of BBV light being controllable by a programmable controller; an image sensor for capturing a plurality of images of a mounted SUT, and one or more sources of UV light mounted within the enclosure. The controller captures images of the mounted SUT from one or more selected angles relative to the sensor elevation axis and relative to the position of the SUT on the stage rotation axis; an image capturing module is configured for processing the one or more images; and, a light grade calculation module is configured for grading the cut/polished SUT using light indicative parameters from at least a part of the one or more images captured.

14 Claims, 8 Drawing Sheets

Related U.S. Application Data continuation of application No. 17/128,044, filed on Dec. 19, 2020, now Pat. No. 11,112,368, which is a continuation of application No. PCT/IL2019/050790, filed on Jul. 14, 2019, which is a continuation-in-part of application No. PCT/IL2018/050777, filed on Jul. 15, 2018.

(51) Int. Cl.

| | |
|---|---|
| *G01N 21/64* | (2006.01) |
| *G01N 33/00* | (2006.01) |
| *G06T 7/11* | (2017.01) |
| *G06T 7/90* | (2017.01) |
| *H04N 23/54* | (2023.01) |
| *H04N 23/56* | (2023.01) |
| *H04N 23/695* | (2023.01) |
| *H04N 23/88* | (2023.01) |

(52) U.S. Cl.

CPC ....... *H04N 23/88* (2023.01); *G01N 2201/061* (2013.01); *G06T 2207/10024* (2013.01); *G06T 2207/20072* (2013.01)

(56) References Cited

U.S. PATENT DOCUMENTS

| | | | |
|---|---|---|---|
| 2006/0066877 | A1 | 3/2006 | Benzano |
| 2011/0228063 | A1 | 9/2011 | Smith et al. |
| 2011/0299063 | A1 | 12/2011 | Ninomiya et al. |
| 2012/0007971 | A1* | 1/2012 | Schnitzer ............. G01N 33/389 |
| | | | 348/61 |
| 2016/0178530 | A1 | 6/2016 | Davies et al. |
| 2016/0290925 | A1 | 10/2016 | Takahashi |
| 2018/0156735 | A1* | 6/2018 | Fitch ........................ G01J 3/462 |
| 2021/0285874 | A1* | 9/2021 | Noda ............... G01N 33/54373 |

OTHER PUBLICATIONS

Search Report—corresponding European Application No. 19838781, dated Mar. 11, 2022, 14 pages.

* cited by examiner

FIG.1B                    FIG.1C

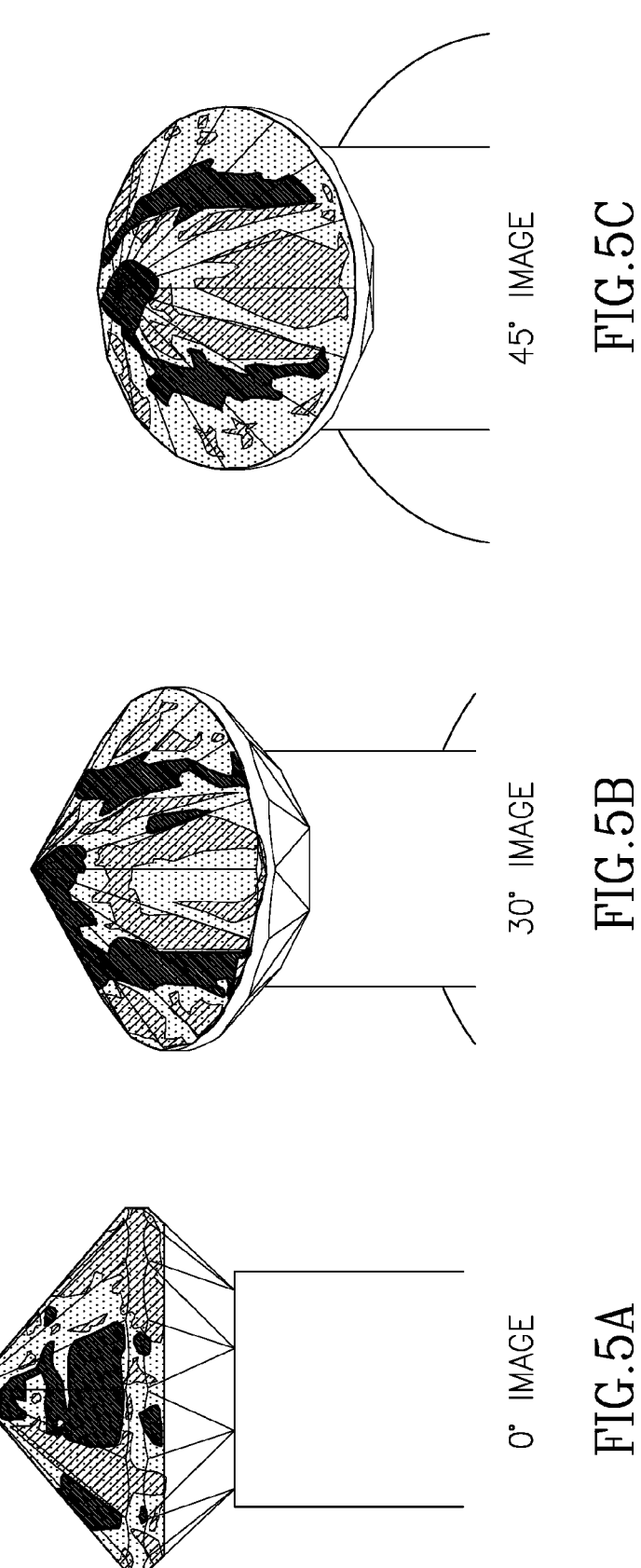
0° IMAGE    FIG.5A
30° IMAGE    FIG.5B
45° IMAGE    FIG.5C

SYSTEM AND METHOD FOR EVALUATING AND DETERMINING COLOR IN GEMSTONES

RELATED APPLICATIONS

This application is a continuation of U.S. application Ser. No. 17/393,654, filed Aug. 4, 2021, which is a continuation of U.S. application Ser. No. 17/128,044, filed Dec. 19, 2020, now U.S. Pat. No. 11,112,368, issued on Sep. 7, 2021, which is a national stage application from PCT Application No. PCT/IL2019/050790, filed Jul. 14, 2019.

BACKGROUND OF THE PRESENT INVENTION

The color of a gemstone, and especially a diamond, is one of its major attributes which affects its value. The less color a diamond has, the higher its value. A perfect crystalline diamond with no structural or chemical impurities is basically colorless. Gemologists judge a diamond's color through visual perception by comparing a diamond of interest in a "color bath" with a set of master stones which define the standard colors on a scale of D to Z, running from colorless to yellow, respectively. For example, a trained gemologist (under ideal standardized lighting conditions) during such comparison will grade a stone color as E if he/she sees the stone in a "color bath" as more yellow than the D master stone but less yellow than the F master stone. There were many attempts to develop a color grading machine to automate the color grading process. Two known strategies to measure color are: colorimetry and spectrophotometry. Shipley offered a colorimetric system having a light source with interchangeable blue and yellow optical filters and a light detector. The optical transmission of filtered light through a target stone could then be measured and compared with a lookup table to grade the stone color along the D to Z scale. One of the main deficiencies of this system was that the light source which did not provide the type of daylight conditions which have been the standard for visual color analysis. Improvements on the Shipley system offered by such entities as Eickhorst, Okuda, Austron and Gran, and although they used more modern light sources and photo detectors, they were designed to direct light into the table and crown.

Spectrophotometers for measuring a diamond color have been offered by Okazaki, Zeiss-Gubelin and later by Rennilson-Hale, Lamdaspec, Gran, Adamas and others. These systems detect and analyze the full spectrum of light. However. They have failed to replace human visual diamond analysis.

GIA U.S. Pat. No. 6,473,164 discloses a technology for color measurement of diamonds based on daylight approximating lighting impinged on the pavilion side of the diamond and then by measuring light coming out of the pavilion at a specific angle. Measurements are compared to historical precedents or converted into CIE color space. According to the '164 patent, a diamond's visual appearance to the human eye under daylight approximating light is a primary indicator of the quality of the diamond.

GIA U.S. Pat. No. 9,678,018 discloses hyperspectral imaging to approximate the visual perception of the human eye by filtering out wavelength ranges which are less perceivable by a human eye.

GIA US publication No. 20160290925 discloses an automated instrument for grading a gemstone's fluorescence color using a UV lighting system to capture fluorescent images of an illuminated gemstone.

De Beers WO2016203210 discloses calculating color vectors from an expression of the chrominance values of a gemstone pixel in chrominance space. The color vector extending in chrominance space from stone pixels having a relatively high luminance value to stone pixels having relatively low luminance values. A direction of the color vector provides a pointer towards the pixels representing light which has travelled along long light paths through the stone and therefore have relatively low luminance.

Sarine 9,519,961—Sarine Loupe—discloses a volumetric 3D model. This disclosure is herein incorporated by reference into this application in its entirety.

U.S. Pat. No. 6,239,867 discloses an apparatus and method for grading, testing and identifying gemstones that includes a number of light sources, including UV light for fluorescence analysis as well as ring lights) mounted within an enclosure to illuminate a mounted gemstone from below and from above. A CCD camera is mounted on a linear positioner to travel from first to second positions to focus the CCD camera the gemstone image.

US 2012/0007971 discloses methods and systems for imaging cut gemstones that includes a number of compact florescent light bulbs or LEDs mounted within a cabinet to provide neutral and homogeneous lighting. There is no mention of providing UV lighting to illuminate a mounted gemstone. An image sensor is mounted on a movable arm that captures images of a mounted gemstone based on illumination from the light bulbs or LEDs.

US 2016/0290925 discloses an apparatus and method for fluorescence grading of gemstones that includes one or more UV light sources and a thermal sensor for adjusting the intensity of the UV light sources.

SUMMARY OF THE PRESENT INVENTION

In an aspect, a system for the automatic grading of a cut/polished diamond or other stone (hereinafter sometimes referred to as a "stone under test" or SUT) includes an enclosure, the enclosure including a holder for supporting the cut/polished stone, the holder comprising a central axis, the holder being rotatable about its central axis by a rotation device; the enclosure further includes one or more sources of broadband visible light (BBV), the sources of BBV light being controllable by a programmable controller, as well as an image sensor for capturing a plurality of color-measurement images of the mounted gemstone; the image sensor is mounted on an actuator for rotation on a plane about the central axis; one or more sources of UV light are mounted on the actuator in the vicinity of the image sensor (or elsewhere), whereby the sensor is programmed by the controller to capture images of the mounted stone from one or more selected angles relative to the sensor axis and relative to the central axis. The controller may be configured to activate the one or more sources of UV light, the one or more sources of BBV light, the rotation device, the actuator and the image sensor to capture one or more color images of the cut/polished stone. The system also may include an image capturing module configured for processing the one or more color images; and, a color grade calculation module configured for color grading the cut/polished stone using color indicative parameters from at least a part of the one or more color images captured.

In another aspect, a method for the automatic grading of a cut/polished gemstone (SUT) includes: providing an enclosure, the enclosure including a stage for mounting the cut/polished SUT, the holder comprising a central axis, the stage being rotatable about a stage rotation axis by a rotation device; the enclosure further comprising one or more sources of broadband visible light (BBV), the sources of BBV light being controllable by a programmable controller; providing an image sensor for capturing a plurality of color-measurement images of a SUT mounted on the stage; the image sensor being mounted on an arm, the arm being rotatable around a sensor elevation axis, the sensor elevation axis being normal to the stage rotation axis; providing one or more sources of UV light within the enclosure; providing an image capturing module configured for processing the one or more images; and, providing a light grade calculation module configured for grading the cut/polished SUT using light indicative parameters from at least a part of the one or more images captured; wherein the method comprises: the controller programming the sensor to capture images of the mounted SUT from one or more selected angles relative to the sensor elevation axis and relative to the position of the SUT on the stage rotation axis; the controller: activating the one or more sources of BBV light, activating the one or more sources of UV light, rotating the SUT around the stage rotation axis, and causing the image sensor to capture one or more images of the cut/polished SUT; the image capturing module processing the one or more images; and, the grade calculation module grading the cut/polished SUT using light indicative parameters from at least a part of the one or more images captured.

In an aspect, the programmable controller is configured to cause the image sensor to capture light in the form of images around the sensor elevation axis from impingement of one or both of the BBV and the UV light sources at a plurality of different angular positions with respect to 0 degrees, wherein 0 degrees is normal to the stage rotation axis of the stage. Further, the controller is configured to cause the image sensor to capture at 0 degrees, at X degrees, and at Y degrees, wherein Y≠X≠0 degrees. Yet further, the controller is further configured to control the power level of the one or more BBV sources, the controller being further configured to cause the image sensor to capture images at more than one power levels of the BBV sources.

In a further aspect, the system further comprises a memory system, and wherein the programmable controller is configured to store the captured images in the memory system for processing. The images captured are stored in the memory system in a RAW format or a non-RAW format.

In yet another aspect, the programmable controller is configured to scan the SUT prior to the controller being configured to capture images for grading, the scan of the SUT causing the controller to create a 3D volumetric model of the SUT. Further, the programmed controller is configured to: (a) for captured image frames, average the color-space values of one or more captured frames to calculate reference values of white balance of the one or more captured frames; and, (b) if a 3D volumetric model of the SUT has been created, select pixels. Also, the controller may be configured to differentiate the selected pixels either by: (a) creating histograms for the selected pixels captured at the different angular positions and by the controller being configured to divide the selected pixels by their levels of intensity, whereby the average color is calculated. (b) segmenting an SUT into distinct regions, and using selected pixels captured within said regions, at the different angular positions, whereby the average color is calculated.

In a further aspect, the controller may be configured to calculate colorspace values of one or more frames of the SUT under the one or more UV light sources, the controller further being configured to add the calculations to the average color calculations from the BBV sources and wherein color grading is corrected based upon measurement under UV illumination. Further, the controller may be configured to compare the average color calculations of a SUT to a calibrated lookup table containing data on calibrated SUTs with known SUT whiteness and to match the SUT calculations to those of the calibrated SUTs to determine a grade level of the SUT.

In an aspect of the method, the programmable controller causes the image sensor to capture light in the form of images from impingement of one or both of the BBV and the UV light sources at a plurality of different angular positions with respect to 0 degrees, wherein 0 degrees is normal to the stage rotation axis of the stage. The controller may cause the image sensor to capture at 0 degrees, at X degrees, and at Y degrees, wherein Y≠X≠0 degrees.

In a further aspect, the programmable controller is configured to further scan the SUT at a central area of the SUT and at least one other area of the SUT. The system of claim 4, wherein the programmable controller is configured to further scan one or more of: (a) at least one peripheral area between the central area and one of the boundaries of the SUT and (b) at least one area above or below the central area.

In yet another aspect, the image sensor may be a color image sensor. The BBV light comprises white light. The system of claim 1, wherein the BBV light comprises a plurality of similar wavelength LEDs producing light in the broadband range. The BBV light comprises a plurality of similar wavelength LEDs producing light in the broadband range. Further, the BBV light may comprise a plurality of dissimilar wavelength LEDs that, when combined, produce light in the broadband range.

In a further aspect, the colorspace values may be RGB values. In addition, the one or more sources of UV may be mounted on the arm in the vicinity of the image sensor.

The one or more sources of UV are mounted on the arm in the vicinity of the image sensor. The step wherein the grade calculation module grading the cut/polished SUT further adjusts the grade calculation based on taking into account the simultaneous contrast effect. Further, the controller is further configured to adjust the operation of the grade calculation module to grade the cut/polished SUT to take into account the simultaneous contrast effect.

In yet another aspect, the one or more sources of UV light are mounted on the stage for mounting the SUT. Also, if a 3D volumetric model has been created, the programmed controller is configured to use the 3D volumetric model to one or more of: (a) adjust one or more of multiple angles set for image capture, (b) determine which of a plurality of sources of UV light to activate, (c) determine which of a plurality of sources of BBV light to activate, and (d) determine the intensity at which to activate each of the selected BBV/UV sources.

In an aspect, the steps of the programmed controller using the 3D volumetric model one or more of: (a) adjust one or more of multiple angles set for image capture, (b) determine which of a plurality of sources of UV light to activate,, (c) determine which of a plurality of sources of BBV light to activate, and (d) determine the intensity at which to activate each of the selected BBV/UV sources. The cut/polished SUT may be a diamond.

In another aspect, a method for the automatic grading of a cut/polished stone (SUT) includes: providing an enclosure, the enclosure including a stage for mounting the cut/polished SUT, the holder comprising a central axis, the stage being rotatable about a stage rotation axis by a rotation device; the enclosure further comprising one or more sources of broadband visible light (BBV), the sources of BBV light being controllable by a programmable controller; providing an image sensor for capturing a plurality of color-measurement images of a SUT mounted on the stage; the image sensor being mounted on an arm, the arm being rotatable around a sensor elevation axis, the sensor elevation axis being normal to the stone stage rotation axis; providing one or more sources of UV light within the enclosure; providing an image capturing module configured for processing the one or more images; and, providing a light grade calculation module configured for grading the cut/polished SUT using light indicative parameters from at least a part of the one or more images captured; wherein the method comprises: the controller programming the sensor to capture images of the mounted SUT from one or more selected angles relative to the sensor elevation axis and relative to the position of the SUT on the stage rotation axis; the controller: activating the one or more sources of BBV light, optionally activating the one or more sources of UV light, rotating the SUT around the stage rotation axis, and causing the image sensor to capture one or more images of the cut/polished SUT; the image capturing module processing the one or more images; and, the grade calculation module grading the cut/polished SUT using light indicative parameters from at least a part of the one or more images captured.

In a further aspect, a method for the automatic grading of a cut/polished gemstone (SUT) includes: providing an enclosure, the enclosure including a stage for mounting the cut/polished SUT, the holder comprising a central axis, the stage being rotatable about a stage rotation axis by a rotation device; providing an image sensor for capturing a plurality of color-measurement images of a SUT mounted on the stage; the image sensor being mounted on an arm, the arm being rotatable around a sensor elevation axis, the sensor elevation axis being normal to the SUT stage rotation axis; providing one or more sources of broadband visible (BBV) light within the enclosure, the one or more sources of BBV light being controllable by a programmable controller; providing an image capturing module configured for processing the one or more images; and, providing a light grade calculation module configured for grading the cut/polished SUT using light indicative parameters from at least a part of the one or more images captured; wherein the method comprises: the controller programming the sensor to capture images of the mounted SUT from one or more selected angles relative to the sensor elevation axis and relative to the position of the SUT on the stage rotation axis; the controller: activating the one or more sources of BBV light, rotating the SUT around the stage rotation axis, and causing the image sensor to capture one or more images of the cut/polished SUT; the image capturing module processing the one or more images; and, the grade calculation module grading the cut/polished SUT using light indicative parameters from at least a part of the one or more images captured.

In another aspect, the BBV light source is controlled with the help of a temperature measuring sensor or sensors. The temperature of the light sources is actively controlled by conventional devices not shown. The temperature of the light sources may be actively controlled to within 1-3° C. or to within 0.1-1° C. The temperature of the BBV light sources is actively controlled to within 0.1-1° C.

In another aspect, the temperature of the UV light sources is actively controlled to within 1-3° C. or to within 0.1-1° C. Also, the temperature of the UV light sources is actively controlled. In addition, the BBV light source is controlled with the help of a light intensity measuring sensor or sensors (not shown). The UV light source is controlled by a temperature measuring sensor or sensors (not shown).

In an aspect, a correction may be applied to the image capturing process, based on a reading from one or more light intensity measuring sensors (conventional and not shown) and a correction is applied is to the image sensor gain, based on a reading from one or more light intensity measuring sensors.

In yet another aspect, the correction may be applied to the image sensor gain, in a known manner, based on a reading from one or more light intensity measuring sensors. A correction applied may be to the image sensor exposure time, based on a reading from one or more light intensity measuring sensors. A correction may be applied to the captured image, based on the reading from one or more light intensity measuring sensors. A correction may be applied to the image capturing process, based on a reading from one or more temperature measuring sensors (conventional but not shown) mounted in or in the vicinity of the enclosure. A correction may be applied to the image sensor gain, based on a reading from one or more temperature measuring sensors. A correction may be applied to the image sensor exposure time, based on a reading from one or more temperature measuring sensors or based on a reading from one or more temperature measuring sensors.

Also, in an aspect, a correction is applied is to the image sensor gain, based on a reading from one or more temperature measuring sensors or to the image sensor exposure time, based on a reading from one or more temperature measuring sensors. A correction may be applied to the captured image, based on a reading from one or more temperature measuring sensors.

In an aspect, any data collected during the measurement under UV illumination may also be used by processing by the controller for grading the fluorescence of the SUT.

In another aspect, a system for the automatic grading of a cut/polished gemstone (SUT) includes an enclosure, the enclosure including a stage for mounting the cut/polished SUT, the stage comprising a stage rotation axis, the stage being configured to be rotatable about the stage rotation axis by a rotation device; the enclosure further comprising one or more sources of broadband visible (BBV) light, the sources of BBV light being controllable by a programmable controller; an image sensor for capturing a plurality of images of a mounted SUT; the image sensor is mounted on an arm, the arm being rotatable around a sensor elevation axis, the sensor elevation axis being normal to the stage rotation axis; one or more sources of UV light mounted on the arm in the vicinity of the image sensor; the sensor is programmed by the controller to capture images of the mounted SUT from one or more selected angles relative to the sensor elevation axis and relative to the position of the SUT on the stage rotation axis; Further, the controller is configured: to activate and control the power level of one or more of the one or more sources of BBV light, to activate and control the power level of one or more of the one or more sources of UV light, to rotate the SUT around the stage rotation axis, to rotate the arm around the sensor elevation axis and to cause the image sensor to capture one or more images of the cut/polished SUT; an image capturing module configured for processing the one or more images; and, a light grade calculation module configured for grading the cut/polished SUT using light indicative parameters from at least a part of the one or more images captured.

In yet another aspect, a method for the automatic grading of a cut/polished gemstone (SUT) includes: providing an enclosure, the enclosure including a stage for mounting the cut/polished SUT, the holder comprising a central axis, the stage being rotatable about a stage rotation axis by a rotation device; the enclosure further includes one or more sources of broadband visible light (BBV), the sources of BBV light being controllable by a programmable controller; providing an image sensor for capturing a plurality of color-measurement images of a SUT mounted on the stage; the image sensor being mounted on an arm, the arm being rotatable around a sensor elevation axis, the sensor elevation axis being normal to the stage rotation axis; providing one or more sources of UV light mounted on the arm in the vicinity of the image sensor; providing an image capturing module configured for processing the one or more images; and, providing a light grade calculation module configured for grading the cut/polished SUT using light indicative parameters from at least a part of the one or more images captured.

The method comprises: the controller programming the sensor to capture images of the mounted SUT from one or more selected angles relative to the sensor elevation axis and relative to the position of the SUT on the stage rotation axis; the controller: activating and controlling the power level of one or more of the one or more sources of BBV light, activating and controlling the power level of one or more of the one or more sources of UV light, rotating the SUT around the stage rotation axis, and causing the image sensor to capture one or more images of the cut/polished SUT; the image capturing module processing the one or more images; and, the grade calculation module grading the cut/polished SUT using light indicative parameters from at least a part of the one or more images captured.

BRIEF DESCRIPTION OF THE DRAWINGS

FIGS. 1B, 1C and 1D graphically illustrate typical power distributions of phosphor-based white LEDs.

FIGS. 5A-5C illustrate another embodiment of another technique for imaging a stone for acquisition of color images taken at 0 degrees, 30 degrees and 45 degrees in the present invention.

DETAILED DESCRIPTION OF THE PRESENT INVENTION

As may be appreciated from the prior art, a gemstone's (and particularly a diamond's) visual appearance to the human eye under natural or daylight-approximating light is the gold standard of the industry when it comes to color grading. As such, existing color measuring devices are based on their ability to approximate daylight lighting and be as close as possible to CIE Standard Illuminant for Colorimetry D65.

These prior art systems generally use incandescent light bulbs such as Tungsten lamps, metal halide lamps, white LED lights, laser induced white light, Xenon flash lamps or fluorescent Halogen lamps having high color temperature (approximately 6500K) and high rendering index (CRI), preferably at least 95. However, no commercially available lamp, as of today, can generate light identical to standardized daylight. Typical "White" LEDs have about 80 CRI and are therefore inadequate to be employed as a source for daylight approximation. Moreover, typical LEDs are characterized by a discrete spectrum with two band spectrum emissions. A first band may occur at about 450 nm and a second band at about 600 nm.

It is to be understood that instead of using a plurality of LEDs with specific light bands in the ranges discussed, a plurality of narrow wavelength LEDs of somewhat differing wavelength ranges may be used, so long as the overall light effect is, when mixed, in the desired broadband.

Figure 1A:
FIG. 1A illustrates an embodiment of the hardware portion of the present invention.
Figure 1D:
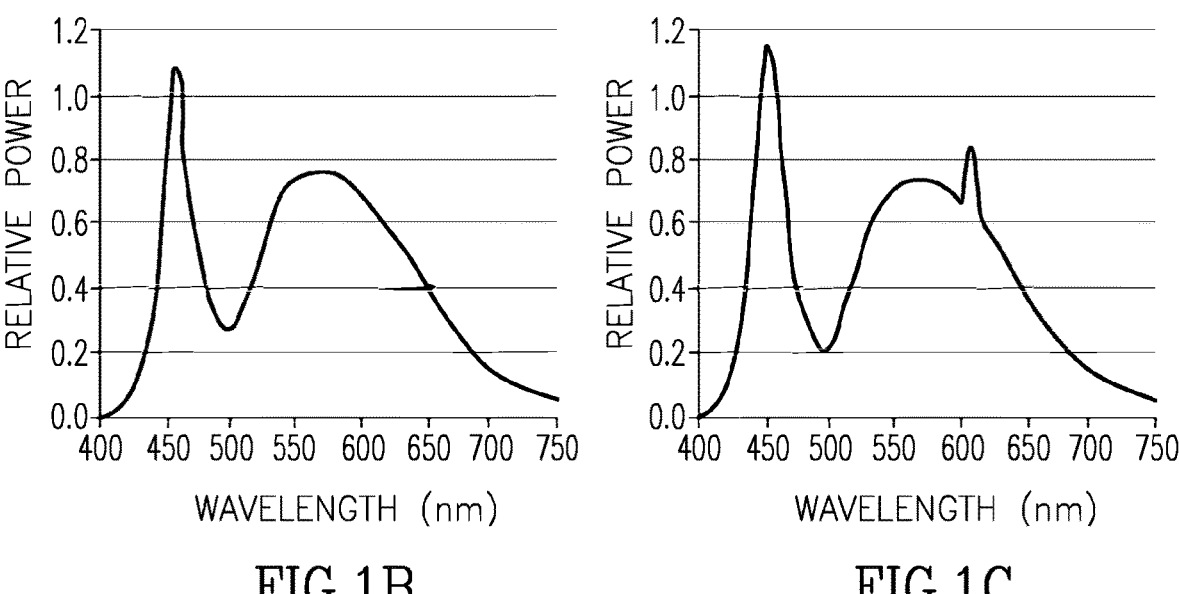

A typical spectral power distribution of phosphor-based white LEDs is shown in FIGS. 1B, 1C and 1D. An automated color grading system which uses such LEDs, however, may underestimate the yellowish color of a diamond and overestimate its grade and value. Therefore, preferably, light from the entire visible spectrum should be used to more accurately grade the color of a diamond, and such light can be obtained by utilizing new LED technology developed for accurate color rendering.

Figure 1D:
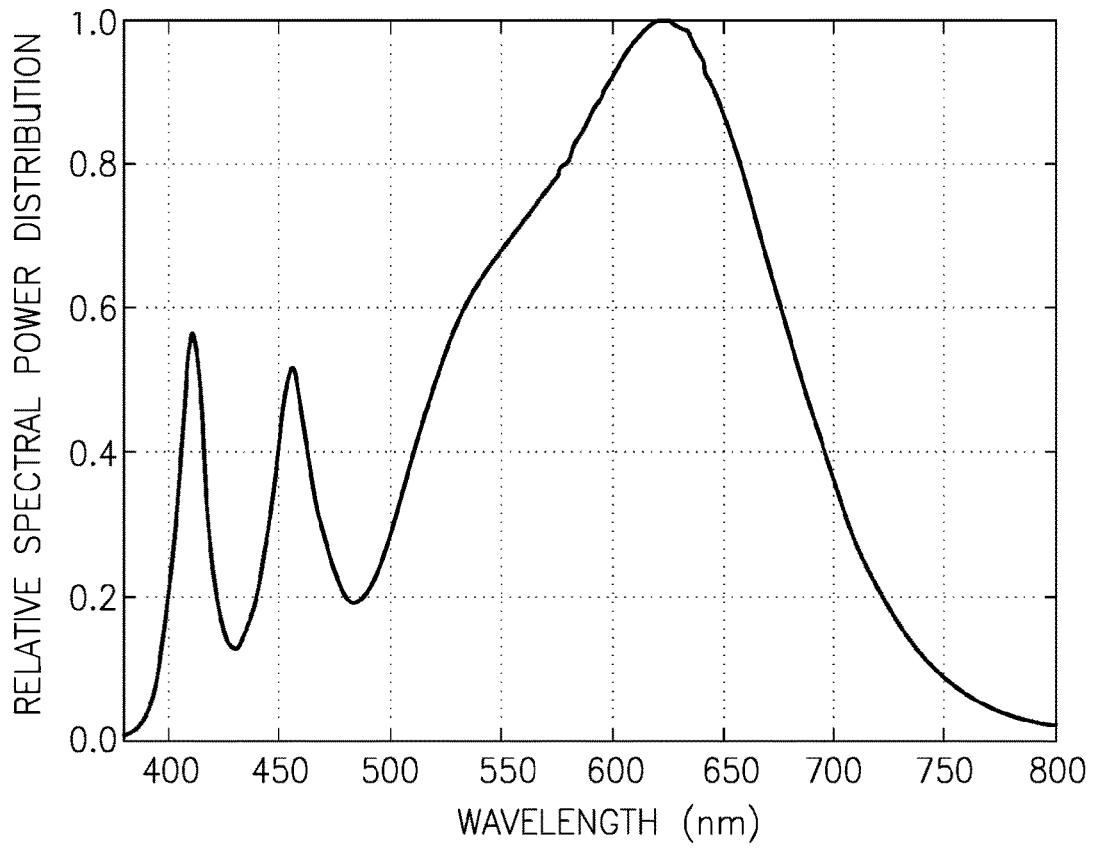

According to this aspect of the invention, and as shown in FIG. 1, there is provided a closed chamber 10 which is configured to hold a gemstone and rotate it on rotatable stage 12. Embedded in the walls of the chamber are arrays of BBV LEDs (not shown) covered by light diffusers 14. Each array of LEDs is controlled by a programmable controller and can be turned on and off separately and is configured to apply dynamic illumination of BBV light with high intensities and homogenously around the centered stone stage. The light generated by the BBV LEDs is used as a base line for color grading process as will be described below.

Furthermore, since in many situations, the illumination surrounding a gemstone may also include non-visible (e.g. UV) wavelengths, which may influence the observer's perception of a stone's color, a color measurement system or method may benefit from incorporating such illumination to account for these otherwise unmeasurable effects. In addition, the closed chamber may include one or more UV LEDs 16A and 16B as seen in FIG. 1A. The UV LEDs 16A and 16B are mounted on a rotatable arm 18 that may rotate on a stone stage rotation axis in directions 15 about a center 20 and a sensor elevation axis and move in directions 19. The UV LEDS are mounted in the vicinity of the sensor 22 and are shown in FIG. 1A as being mounted on either side of the sensor. However, the LEDs may be mounted anywhere else within the enclosure suitable so that the stone is adequately illuminated by the LEDs, including mounting the LEDs or some of the LEDs on the stage itself.

A camera or other type sensor 22 may be mounted near to the LEDs 16, may move on a sensor focusing axis in directions 23 to capture images from a diamond or other gemstone (not shown) mounted on the top portion 17 of rotating stage 12. In this manner, the LEDs 16A and 16B with camera or sensor 22 may rotate around center 20 in directions 19 on the sensor elevation axis and capture images from a mounted gemstone at a variety of angles, to be discussed below. A benefit of this arrangement is that the light emitting from the UV LEDs is better directed to reflect UV light back from the SUT at all the positions the sensor 22 is movable about the SUT than if the UV LEDs were mounted elsewhere within the chamber, such as along the inner walls of the chamber.

A diamond's color differences along the D to Z scale are very small and are usually seen by a professional, trained and experienced expert. In particular, color differences between D to F grades are very close. However, differences in grades D to F possess very dramatic effects on a stone's price. Color differences are calculated in color space as $\Delta E$. $\Delta E$ is appreciated as reflecting a just noticeable difference (JND) and unempirically valued by CIELAB as 1. However, the difference between diamond color grade D and E is about 0.6 $\Delta E$ which is less than the JND for average persons.

In other words, the average person will see and perceive diamonds graded as D and those graded as E in much the same way, although their prices are very different. A conventional color image sensor is no better than a human eye in discerning color differences.

It is therefore another aspect of the present invention to use an image sensor with improved radiometric resolution. Moreover, using a regular viewing screen there is no way to present the measured data and it is another aspect of the invention (to be described below) as to the ways that the raw data is processed, analyzed and eventually provides an accurate color grading for a gemstone.

Another aspect of the present invention is 3D volumetric modeling of the diamond. This modelling, which may or may not be used in connection with the invention of the present invention, is described in the aforementioned U.S. Pat. No. 9,519,961, which is incorporated by reference herein in its entirety. Obtaining a volumetric model of the SUT may be beneficial in evaluating the color of that same stone when specific areas of the stone are used for such color evaluation as will be described below.

Gemologists grade a diamond color based on the light emitting from the pavilion after a single reflection-so-called "clean" light. Multiple internal reflected light beams may have different color tones and therefore less accurately represent the real color of the diamond. Therefore, according to this aspect of the invention the color grading system may measure single reflected light for the color evaluation. Based on the 3D model as mentioned above, or other image processing modelling, stone masks are calculated from which color evaluation may be done.

As the color of a diamond is a deciding factor in its value, there is considerable financial motivation to circumvent any automated color evaluating system in order to apply a higher grade. One easily implementable, and therefore potentially common approach for this type of fraud would be to measure the color of a higher grade stone and attribute it to another, or many other lower grade diamonds. Therefore, in another aspect of this invention, the system would possess means by which to verify the identity of the SUT. This could be accomplished, for example, by utilizing the 3D volumetric model of the SUT and comparing it to a known reference for the same stone. Another possible method by which to verify the identity of the SUT would be to read an inscribed code on the girdle of the diamond. Yet another method could be to compare surface features of the SUT to a known reference. Any, or any combination of these approaches for stone traceability could be used to a) identify the diamond before and during scanning, b) record the uniquely identifiable information of the diamond, and c) verify its identity at a future point in time, thus greatly reducing the opportunity for grading fraud. One system and method of uniquely identifying a gemstone is U.S. application Ser. No. 15/564, 565, filed Oct. 5, 2017, assigned to the assignee of the present invention, the entire contents of which is herein incorporated by reference.

A First Embodiment to Determine Color

In a first embodiment, one specific methodology to determine color includes the following general steps:

(1) first scanning a cut/polished diamond or other stone to capture a first plurality of images at different positions of the cut stone about its stage's rotational axis, and using these images to calculate a volumetric 3D model of the stone, for example, using the techniques disclosed in the aforesaid U.S. Pat. No. 9,519,961, and (2) next, performing a second scanning of the cut diamond at an angular position of the image sensor which may be different from that in the first scanning, to capture a second plurality of images at different positions of the cut stone about its stage's rotational axis, then processing these images by an image capturing module within the system, using at least a part of volumetric data derived from the images obtained in the first scanning.

As used herein, the first scanning will be referred to as 'modeling scanning'. The first images used to calculate a volumetric/3D model of the diamond will be referred to as 'modeling images'. The second scanning will be referred to as 'color-measurement scanning' and the second images used for color determination It will now be described how areas are selected in the image of the cut/polished diamond in each color-measurement image, by the image capturing module, when it processes the color-measurement images, for the use of color indicative parameters of these areas in the measurement of the cut/polished diamond's color.

First, each selected area has a closed circumference separating it from the remainder of the image of the cut stone and, optionally, from the background image or holder image, in case a portion of the above circumference coincides with a corresponding portion of the respective boundary of the image of the cut/polished stone in the color-measurement image. Each of the selected areas can be analyzed individually or in conjunction with another area.

Second, the areas which may be selected may, for example, include a central area, and at least one additional area, the additional area being optionally constituting either at least one peripheral area disposed between the central area and one of the above boundaries, or an area disposed above or below the central area. It is to be noted here that what is considered to be a "central area", a "peripheral area" and a "boundary" may be affected by the physical structure of the stone itself as well as perhaps by the 3D model of the stone itself.

The use of the combined selection of the central area with at least one additional area for color grading of a cut diamond, according to the presently disclosed subject matter, is connected to the surprising effect that such selection achieves a more accurate result than that obtained based solely on selection of a central area, i.e. a result that is closer that obtained by a human eye during color grading. One possible explanation to this surprising effect is presented below.

It is known that determining a color of a diamond is normally performed by examining a central area of its part remote from its table facet, such as a central area of a pavilion in a round cut diamond. This central area is considered to reflect the true color of the diamond, since it has the least internal reflections when looking through its side and thus has the brightest color and which best represents the true structure of the diamond.

However, the human eye can be expected to be affected during the examination of the central area by the color of the areas adjacent the central area, due to a phenomena known as the 'simultaneous contrast' effect, which is the enhancement or diminishment, relative to normal, of perception, cognition or related performance as a result of simultaneous exposure to a stimulus of lesser or greater value in the same dimension (here, normal perception, cognition or performance is that which would be obtained in the absence of the comparison stimulus—i.e., one based on all previous experience).

Figure 4:
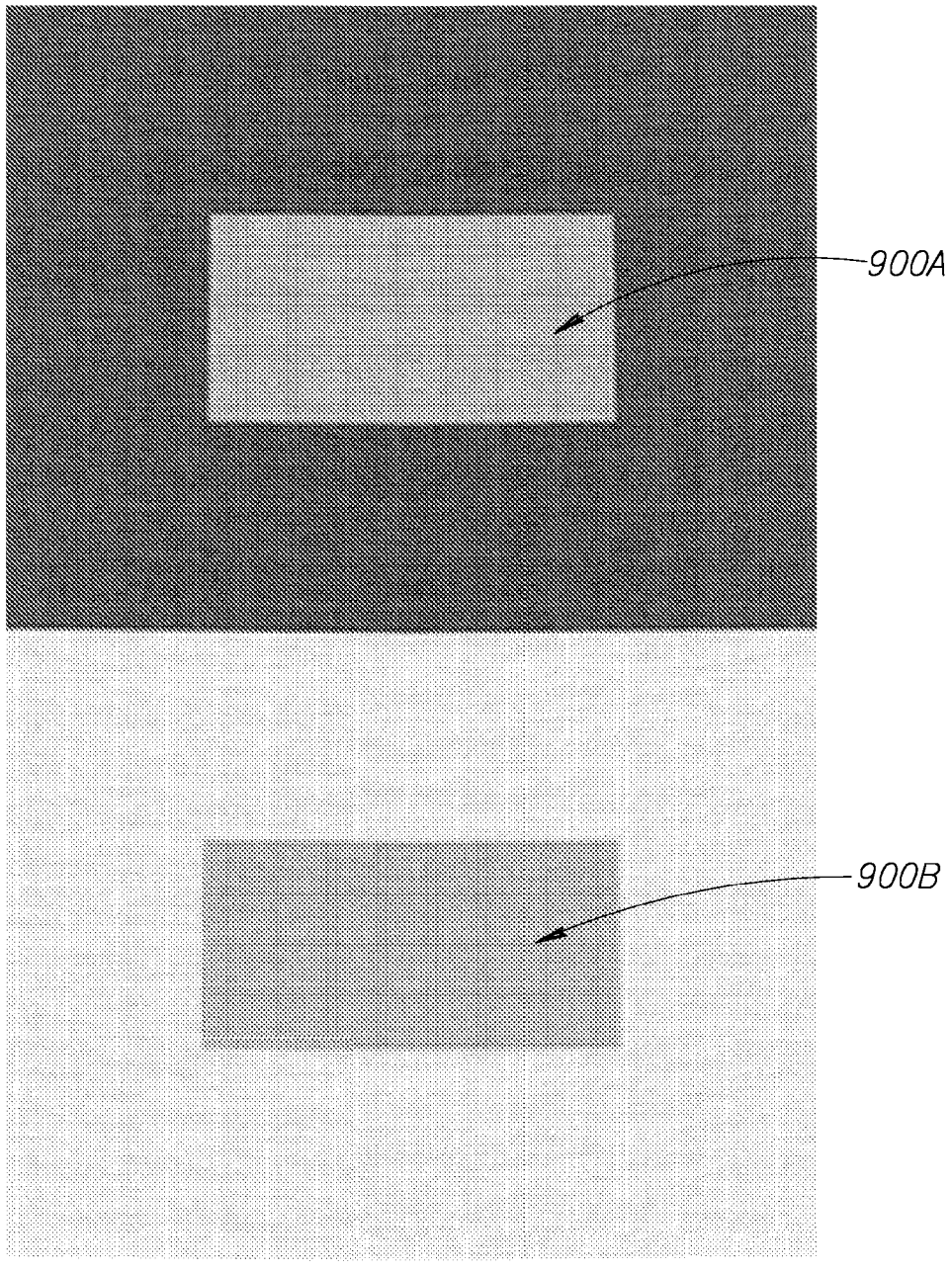
FIG. 4 is a graphical illustration of a phenomena known as the "simultaneous contrast effect".

FIG. 4 exemplifies this "simultaneous contrast" phenomena by illustrating two identical grey rectangles, an upper rectangle 900*a* and a lower rectangle 900*b*. Each of these rectangles is surrounded by a background, a dark and a light background respectively. To the human eye, the upper rectangle 900*a* appears to be a lighter grey than the lower one due to the different backgrounds.

When selecting the central and additional areas, the uppermost surface of the stage, which is in contact with the surface of the gemstone, can be used as a reference plane, and the 3D model of the gemstone in the stage can be used to determine in the color-measurement images the real position of this plane. In general, any surface of the stage, or other element of the system that can be seen in both modeling and color-measurement images can be used as a reference plane.

In each of the color-measurement images, real position of elements of the cut stone in its image can first be identified, based on the corresponding data obtained from the 3D model, and this identification, combined with the knowledge of the position of the reference plane, can allow applying a unified approach to the division of the images of the cut diamond in the color-measurement images into the above areas for a further analysis of its color.

Geometrical or other considerations, based on which dimensions of the central and additional areas can be determined can be, for example, distances of the selected area from specific elements of the cut stone or its boundaries.

Each of the central and/or additional areas can be defined by geometric definition of its location/size relative to a specific dimension/s of the cut diamond, such as e.g. the height of the pavilion in a round cut diamond (i.e. the distance between the girdle and the culet of the diamond), its maximal width (the length of its girdle in a plan view) In particular, each area can be defined to extend between a fifth to a third of the maximal width of the cut diamond and/or between three and one quarters of a distance between a plane passing through the diamond at its location of a maximal width and its extremity disposed at a maximal distance from its table facet, such as a distance between the respective girdle and culet of a round cut stone. The additional area can have the same height relative to the reference plane as the central area and can have a total length along this plane greater than that of the central area For example, in the pavilion of a round cut diamond, the central area can be selected to extend along a majority of the height of the stone between its girdle and culet, and optionally its spacing from the culet can be greater than that from the girdle. The "central" area can also be found to be asymmetrical, or furthermore, non-contiguous and even not actually around the center of the stone but calculated by an alternative method that may apply analytical image processing tools.

The color indicative parameters can be used in any calculative combination, e.g. using one or two-color indicative parameters from one area with one or two-color indicative parameters from another area to obtain a color grading. The color grading can be a result of averaging a number of such combinations.

Figure 2A:
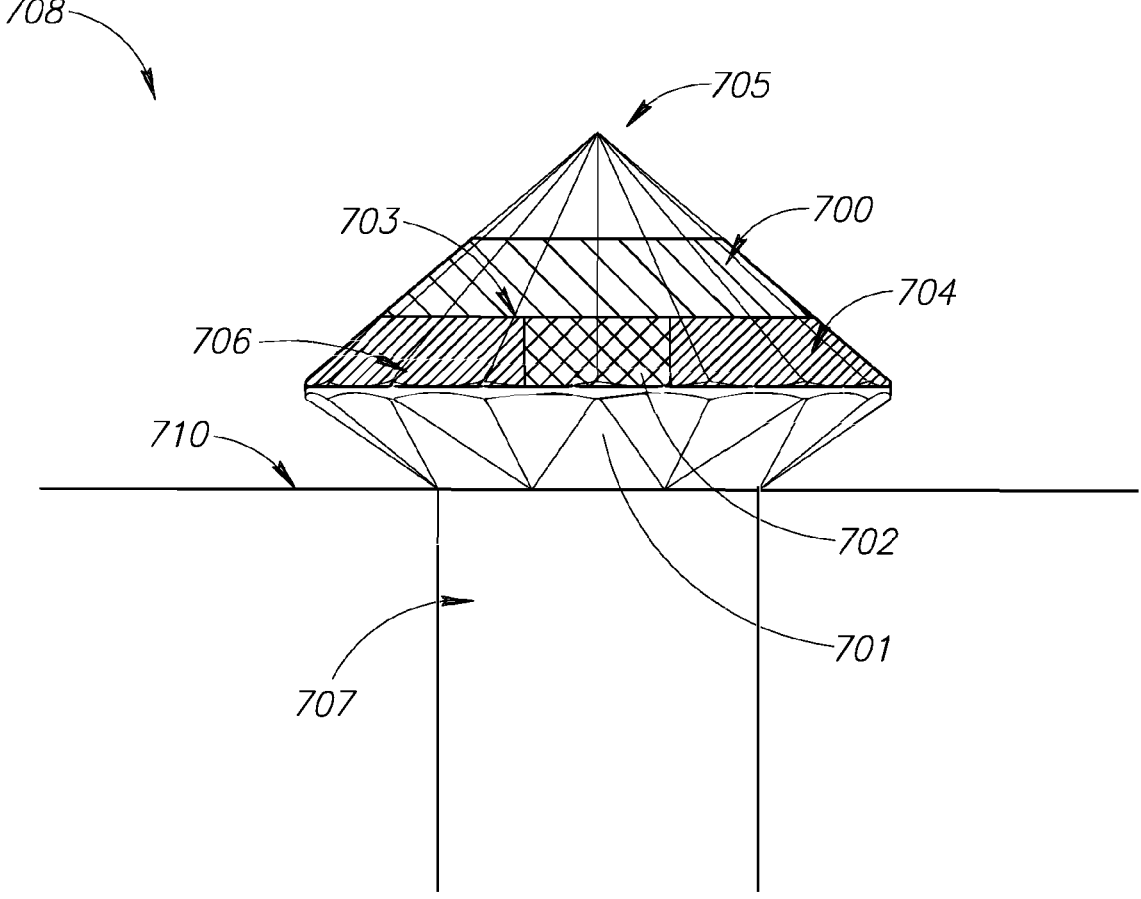
FIGS. 2A through 2C illustrate one embodiment of a technique for imaging a stone to determine volumetric characteristics.
Figure 2B:
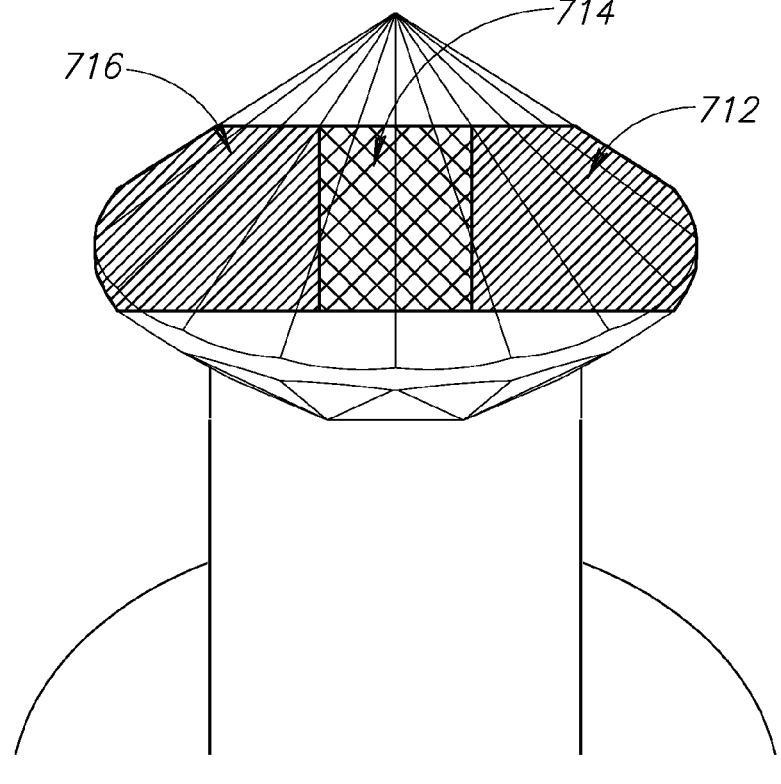
Figure 2C:
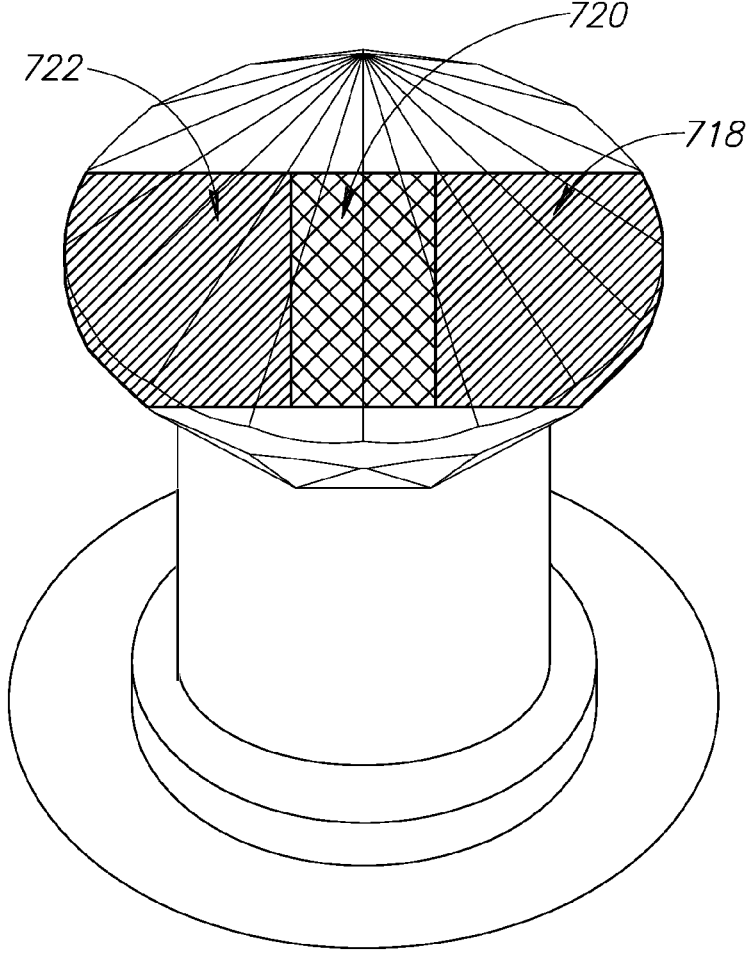

FIGS. 2A to 2C each illustrate one color-measurement image taken by the image sensor at the following respective angles mentioned above: 0°, 30°, and 45, each including an image of a round cut diamond 705, an image of a stage 707 supporting it so that its girdle and pavilion are disposed above the stage, an image of the background including a background reference 708, and a reference plane 710. It is to be understood that the present invention is not limited to measurements at the above angles and any other suitable angle or set of angles may be implemented.

Referring to FIG. 2A, the image of the cut diamond 705 is shown therein to be completely above the reference plane 710. In this image, the zones of interest are an upper zone 700 constituting an upper selected area, and a lower zone 701 divided into a central area 702 and two peripheral areas 704 and 706 on two sides of the central area, the upper and peripheral areas constituting additional selected areas. The upper and lower areas are separated by a border line 703 and are selected so that each extends along a third of the distance between the girdle and the culet. The upper third of said distance in this example is not considered as an area of interest. The central and peripheral areas are selected so that each extends along one third of this border line 703. In this specific example the upper area 700 and the central area 702 each yield separate color indicative parameters while the peripheral areas 704 and 706 can be treated as a single additional area and therefore yield color indicative parameters summarized from both areas together.

In FIGS. 2B and 2C, the pavilion of the diamond as seen in the respective images thereof comprises only three selected areas, a central area 714, 720 and two peripheral areas 712 and 716, 718 and 722, respectively. The color indicative parameters derived from these images are obtained taking similar measures as elaborated above in connection with FIG. 2A.

Figure 3:
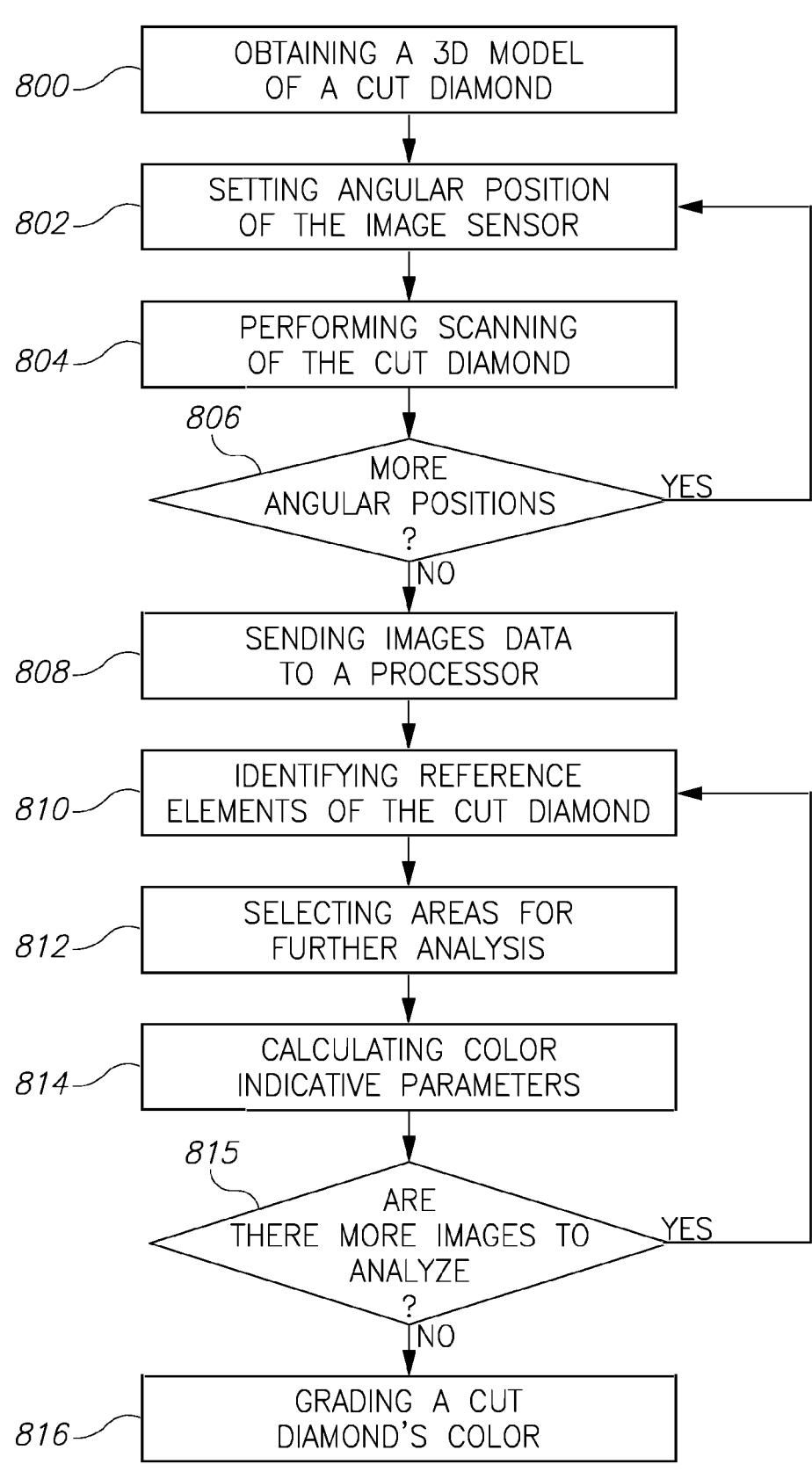
FIG. 3 is a flow chart of a series of operations on a SUT to determine its color characteristics.

Color assessment of a diamond can be performed in accordance with this first embodiment as illustrated in FIG. 3.

First, a 3D model of the cut diamond is obtained in step 800. The 3D model can be obtained, for example, by a modeling scanning of the cut stone. FIG. 3 shows one example of how a plurality of modeling images acquired at different positions of the diamond about the rotational axis of its stage in accordance with the teachings of the '961 patent or another technique. An image sensor is then set in step 802 at a desired angle of its optical axis relative to the horizon for color-measurement scanning of the cut diamond, which is then performed in step 804 by a relative movement of the cut diamond with respect to the image sensor, to capture color-measurement images of the cut diamond at different positions about the rotational axis of the stage. The scanning of the cut diamond in step 804 can be performed at a number of angular positions of the image sensor and for each such position determined in step 806, steps 802 and 804 are repeated.

The captured images are sent in step 808 to an image processing device which can be an image capturing module of the kind used in the system described in the aforesaid U.S. Pat. No. 9,519,961 or any other processor, provided with an appropriate software for a further analysis. It should be noted that the images can be sent to the image processing after any of the previous steps, for example immediately after being captured or at the end of the color measurement scanning.

Steps 810 to 815 relate to the image processing. More particularly, in step 810 reference elements of the imaged cut diamond and/or its stage are identified in each image of interest for color grading, typically based on the obtained 3D model. Such elements can be boundaries of the cut diamond, the stage reference plane, the diamond's girdle and/or culet or the like. Once the reference elements are identified, areas in the cut diamond are selected in step 812 based on geometrical definitions, such as distances between the reference elements. Each selected area in the images contains data relating to color, namely color intensity values within the pixels assembling the selected area. These values are analyzed and calculated by methods known in the art to obtain at least one-color indicative parameter step 814. Steps 810, 812 and 814 are repeated for each image that needs to be analyzed according to step 815.

A color grade of the cut diamond is calculated step 816 using the obtained color indicative parameters. The color grade is obtained by a calculative combination of different color indicative parameters from different areas, optionally giving each color indicative parameter a different weighting factor color.

While the above discussion details one method of measuring color by using first a 3D volumetric measurement of the stone, followed by selective imaging of the stone, other ways may be utilized. In fact, a 3D analysis may be eliminated altogether, so long as some methodology is utilized so that the stone' boundaries are known.

A Second Embodiment To Assess Stone Color

The hardware setup of the device used in connection with the present invention was briefly discussed above in connection with FIGS. 1A and 1B. As discussed, two types of light sources are made to impinge on the stone, surrounding BBV light and also UV light sources mounted close to the camera. While two types of light sources are shown and discussed, it is within the present invention to implement more than two types of light sources. While two UV LEDs are shown in FIG. 1, it is to be understood that more than or for that matter less than two UV sources may be implemented and used. Also, while the UV light sources are illustrated as being placed on either side of the camera in FIG. 1, it is to be understood that they may be placed within other areas in the cabinet shown in FIG. 1.

In operation, the stone may be homogeneously and diffusely illuminated from all sides, by the LED pixeled panels, all of which may be controlled independently. The illumination is made so that it is similar from all sides, as much as possible. The illumination may be controlled manually or may be controlled automatically through the placement of light sensors within the cabinet that are operatively connected to the programmable controller mentioned above. In operation, the user of the system may input, depending on the stone characteristics for example, different parameters of lighting schemes. These schemes may be developed empirically through use of the color system and stored in a non-volatile memory for use in discerning color of stones under test (SUT). Also, while it is expected that uniform, homogeneous, diffused illumination will be implemented to provide lighting by the LEDs, it may be preferable in certain circumstances or conditions depending on the stone itself to provide less homogeneous and more directional lighting by the LEDs.

BBV light can be white light, with sufficiently high correlated color temperature (CCT) and sufficiently high color rendering index (CRI), which has an appropriate and satisfactory continuous representation for all visible wavelengths within the 400-700 nm range, and no significant gaps in the visible spectrum, D65-specified color or spectrum (daylight approximation) are not necessary.

The light produced by the LEDs is not "daylight approximating" and is not near the D65 standard. The D65 standard is known formally as CIE Standard Illuminant D65 and is a commonly used standard illuminant, even though there are not really any light sources that operate at this standard.

Returning now to FIG. 1, the stone may be first mounted on the rotating stage 12 and then it is illuminated, while it is mounted on the rotating stage in a table-down position, to ensure illumination through the stone's pavilion. The stone is then rotated by the rotating stage around its axis.

To improve the repeatability of the illumination and to produce consistent measurement across a variety of stones, the stone is preferably centered, that is, the stones' rotational symmetry axis or center of mass is aligned with the stage axis of rotation.

As mentioned above, in addition to BBV illumination using the LEDs discussed above, UV LEDs (365 nm) may be included in the optical setup, either directly illuminating the stone or illuminating the stone indirectly through suitable lenses or reflector or both. Also, while UV lights of 365 nm wavelength are given above, it is to be understood that UV lights of other wavelengths may be used and, as mentioned, more than or less than two UV LEDs (of different wavelengths) may be implemented, and, further, may be mounted at positions within the cabinet at other places than on either side of the camera.

The procedure for evaluating the color of a stone under test (SUT) may be taken in two major steps, the first being data acquisition and the second being an analysis of the data acquired in the first step.

Step 1: Data Acquisition

As can be seen by referring to FIG. 1, the camera or sensor and associated UV lights are mounted for rotation about an axis 20 that allows the camera to capture images of the SUT at various angles. This may be accomplished while the SUT is stationary or as it is rotated by the rotating stage 12.

The light from the impingement of the UV and other light sources is collected by the sensor or camera 22 through its lens system. The camera and the camera optics may be constructed so that even slight differences in color may be distinguished.

In one embodiment example, the camera may take multiple pictures (frames) at each of the several different angular positions: 1. At 0° (normal to the rotation axis of the rotating stage 12) with BBV illumination; 2. At an elevation (towards the culet) with BBV illumination. 3. At a different, higher elevation (towards the culet) with BBV illumination. 4. At 0° (normal to the rotation axis) with UV illumination with power level 1.5. At 0° (normal to the rotation axis) with UV illumination with power level 2. Exemplary images taken at these angles are illustrated in FIGS. 6A-6C.

It is to be appreciated that the several angles and application of two power levels are only exemplary. Images may be captured at multiple angles, depending at least in part to the size and the shape characteristics of the SUT. For example, the "initial" angle may not be 0 degrees at all, but something other than 0 degrees, dependent on the geometry of the SUT, which in turn may be determined by 3D volumetric modelling of the SUT. Also, more than or less than three angle image captures may be obtained. Also, by employing multiple power levels, is considered only as optional, since as one power level may well suffice.

A total of 300 (or more, or less) images may be captured. It is to be understood that is not necessarily the minimal number nor a maximal number, and in theory, this number can be changed to suit the characteristics, for example, of the SUT. The images captured may then be stored in RAW format with no image processing (e.g., white balance) applied to those images. While the RAW format is the preferred format, the present invention is not limited to such format and other formats may be applied. The captured images may be stored in a suitable memory systems or device under the control of the programmable controller.

Additionally, before data acquisition and as discussed above, the stone may be scanned to create a 3D volumetric model of it (by using the techniques discussed above such as the silhouette modeling method). This model will be used to determine which of the pixels (in the future measurement) are within the stone, and which are not. Also, the 3D model may determine the total (optimal) number of images, best appropriate angular elevations of the sensor and power levels of the BBV and UV illumination. This is due to the possibility of different optimal methods for measurement of different 3D models (shape and size of the stone).

Further, Since the 3D volume and/or the geometry of the stone may determine and influence the images to be captured, the 3D model created may be utilized to provide the controller information with which to adjust one or more of the multiple angles set for the image capture. In addition, such model may be utilized to determine which of a plurality of LEDs to activate or not activate.

Step 2: Data Analysis and Feature Extraction

As a first substep, the data acquired during step 1. above, consisting of raw images, may be then probed to recover the relevant pixels to be considered and analyzed.

First, the white reference is taken. The R, G, and B values are averaged to obtain the reference values for white balance of the specific frame. This may be performed only using BBV-illuminated pictures, and not for UV-illuminated pictures.

Second, the pixels within the stone may be selected by using the optimized stone masks calculated from a 3D volumetric model, if employed earlier, and using, for example, the techniques disclosed in the aforesaid U.S. Pat. No. 9,519,961.

The stone pixels' colorimetric values are then calculated in the following manner: It is noted that the calculation may use white balance correction for every frame.

For the UV-illuminated frames' R, G, and B values can be taken without any reference of calculation.

The stone pixels taken with BBV illumination can be differentiated according to different histograms: one for each of the several (e.g., three) camera angles, or, as mentioned above other suitable angles and in more than or less than three angles. The groups are separated by intensity levels for every camera angle (for all 60 frames).

It is to be noted here that the foregoing technique may be used in lieu of forming a 3D volumetric model of the stone, an example of which technique is disclosed in the aforesaid U.S. Pat. No. 9,519,961 mentioned just above.

For each group of pixels, the average color values given from the above calculations, standard deviations, and number of pixels for this group is calculated Additional to the BBV illumination light values, the UV-illuminated R, G, and B values, standard deviations, and number of pixels are added for both UV intensities. Together, these are the featured values that provide the desirable information for the analysis of color in a given SUT.

Additional values may be calculated from the UV features captured by the camera: those of intensity and the color of fluorescence. Furthermore, these values could be used to grade SUT fluorescence, in line with well-established manual methods.

All of the foregoing may be analyzed by a processor under the control of the programmed controller to provide a measure of the color of the SUT.

One key aspect of any measurement device is its ability to reproduce previous results, otherwise termed "repeatability". This is especially the case when grading diamond color, as even small variations can have a significant effect on the price. As such, it would be of particular interest to ensure that the conditions under which measurements occur are tightly controlled, namely the conditions governing the operation of the LEDs and imaging sensor. For both components, the primary source of variability has been shown to be temperature, which affects the gain and background noise of the sensor, and the power and wavelength of the LEDs. Therefore, in one embodiment, the temperature of the LEDs and of the imaging sensor are controlled via closed loop systems, such as, but not limited to those based on thermoelectric cooling, phase change material, or resistive heating to a predefined, above ambient temperature. In an additional embodiment, which can further be combined with the temperature control methods listed here, the temperature of the LEDs and sensor are monitored, and a correction is applied in software for any changes. This correction can be implemented by any number of standard means, including, but not limited to, look up tables and analytical functions.

In addition, as LED output can degrade over time, it is very advantageous to monitor this directly. Therefore, in another embodiment, which can also be implemented in conjunction with the methods listed above, the device will include photodiodes dispersed throughout the enclosure to monitor the outputs of the LEDs. Changes in LED output can then be corrected by any combination of: closed loop control of the LED currents, changes to the camera gain and/or exposure time or multiplying by a correction factor in software. Such correction can be applied to either or both the visible light and the UV LEDs.

What we claim is:

1. A method for comparing a stone under test (SUT) to a plurality of saved SUT data, the method comprising:

providing an enclosure, the enclosure including a stage for mounting the SUT, the stage comprising a stage rotation axis, the stage being rotatable about the stage rotation axis by a rotation device;

capturing, by one or more provided image sensors, a first plurality of SUT images at different positions about the stage rotation axis and a sensor elevation axis;

illuminating the SUT with:

one or more broadband visible (BBV) light sources stationary with respect to the one or more image sensors; and one or more ultraviolet (UV) light sources configured to move with the one or more image sensors;

capturing, by the one or more image sensors, a color indicative plurality of images at different positions about the stage rotation axis and the sensor elevation axis while illuminating the SUT from different angles or elevations;

characterized in that:

the one or more image sensors are mounted on a movable arm, the arm being rotatable around the sensor elevation axis at a variety of angles to capture images of a mounted SUT, the sensor elevation axis being normal to the stage rotation axis;

the one or more UV light sources being mounted on the arm in the vicinity of the one or more image sensors;

generating, by a programmable controller, (i) an SUT 3D volumetric model of the SUT from the first plurality of images, (ii) an SUT color measurement based on the 3D volumetric model and the color indicative plurality of images, and (iii) SUT data based on the SUT 3D volumetric model and the SUT color measurement; and comparing, by the programable controller, the SUT data to the plurality of saved SUT data of one or more stones; and generating a match, by the programable controller, between the SUT and a specific stone of the one or more stones when a predefined matching criterion occurs between the SUT data comprising the SUT 3D volumetric model and the SUT color data and the plurality of saved SUT data comprising the SUT 3D volumetric model and the SUT color data of the specific stone of the one or more stones.

2. The method according to claim 1, wherein the SUT is in a polished state.

3. The method according to claim 1, further comprising:

illuminating the SUT by the one or more UV light sources to obtain a UV color indicative plurality of images at different positions of the SUT about the stage rotation axis of the SUT; and processing the UV color indicative plurality of images to update the SUT color measurements.

4. The method according to claim 3, further comprising:

processing the UV color indicative plurality of images, by said programmable controller; and generating SUT fluorescence color data to form part of the SUT data.

5. The method according to claim 3, further comprising controlling temperature of at least one of the one or more broadband visible (BBV) light sources or one or more UV light sources.

6. The method according to claim 5, wherein controlling the temperature comprises controlling the temperature to within 1-3 degree Celsius or to within 0.1-1 degree Celsius.

7. The method according to claim 1, further comprising; correcting, based on a temperature measurement obtained in the vicinity of the image sensors and by the programable controller, one or more of the following: capturing images, gain of the image sensor(s), and exposure time of the image sensor.

8. A system for comparing a stone under test (SUT) to a plurality of saved SUT data, the system comprising:

an enclosure, the enclosure including a stage for mounting the SUT, the stage comprising a stage rotation axis, the stage being rotatable about the stage rotation axis by a rotation device;

one or more image sensors configured to capture a first plurality of SUT images at different positions about the stage rotation axis and a sensor elevation axis;

illuminating the SUT with:

one or more broadband visible (BBV) light sources stationary with respect to the one or more image sensors; and one or more ultraviolet (UV) light sources configured to move with the one or more image sensors;

capturing, by the one or more image sensors, a color indicative plurality of images at different positions about the stage rotation axis and the sensor elevation axis while illuminating the SUT from different angles or elevations;

characterized in that:

the one or more image sensors are mounted on a movable arm, the arm being rotatable around a sensor elevation axis at a variety of angles to capture images of a mounted SUT, the sensor elevation axis being normal to the stage rotation axis;

the one or more UV light sources being mounted on the arm in the vicinity of the one or more image sensors;

generating, by a programmable controller, (i) an SUT 3D volumetric model of the SUT from the first plurality of images, (ii) an SUT color measurement based on the 3D volumetric model and the color indicative plurality of images, and (iii) SUT data based on the SUT 3D volumetric model and the SUT color measurement; and comparing, by the programmable controller, the SUT data to the plurality of saved SUT data of one or more stones; and generating a match, by the programable controller, between the SUT and a specific stone of the one or more stones when a predefined matching criterion occurs between the SUT data, comprising the SUT 3D volumetric model and the SUT color data and the plurality of saved SUT data comprising the SUT 3D volumetric model and the SUT color data of the specific stone of the one or more stones.

9. The system according to claim 8, wherein the SUT is in a polished state.

10. The system according to claim 8, wherein the programable controller is further configured to:

illuminate the SUT by the one or more UV light sources to obtain a UV color indicative plurality of images at different positions of the SUT about the stage rotation axis of the SUT; and process the UV color indicative plurality of images to update the SUT color measurements.

11. The system according to claim 10, wherein the programable controller is further configured to:

process the UV color indicative plurality of images; and generate SUT fluorescence color data to form part of the SUT data.

12. The system according to claim 10, wherein the programable controller is further configured to:

control temperature of at least one of the one or more broadband visible (BBV) light sources or one or more UV light sources.

13. The system according to claim 12, wherein the control of the temperature comprises controlling the temperature to within 1-3 degree Celsius or to within 0.1-1 degree Celsius.

14. The system according to claim 8, wherein the programable controller is further configured to:

correct, based on a temperature measurement obtained in the vicinity of the image sensors, one or more of the following: capturing images, gain of the image sensor (s), and exposure time of the image sensor.

* * * * *